United States Patent [19]

Penrose et al.

[11] Patent Number: 5,792,089
[45] Date of Patent: Aug. 11, 1998

[54] WOUND DRESSING

[75] Inventors: Jane Edith Penrose, Skipton, United Kingdom; Alan Stanley Neil, Indian Shores, Fla.

[73] Assignee: Smith & Nephew PLC, London, England

[21] Appl. No.: 530,361

[22] PCT Filed: Apr. 12, 1994

[86] PCT No.: PCT/GB94/00764

§ 371 Date: Jan. 22, 1996

§ 102(e) Date: Jan. 22, 1996

[87] PCT Pub. No.: WO94/23678

PCT Pub. Date: Oct. 27, 1994

[30] Foreign Application Priority Data

Apr. 13, 1993 [GB] United Kingdom ............ 9307624

[51] Int. Cl.⁶ ........................................ A61F 5/00

[52] U.S. Cl. ............................. 602/42; 602/47; 602/57; 128/888

[58] Field of Search ................ 602/41–59, 421; 128/888, 889

[56] References Cited

U.S. PATENT DOCUMENTS

| | | | |
|---|---|---|---|
| 4,641,643 | 2/1987 | Greer | 128/888 |
| 4,733,659 | 3/1988 | Edenbaum et al. | 602/57 X |
| 4,917,112 | 4/1990 | Kalt | 128/888 X |
| 5,060,662 | 10/1991 | Farnsworth, III | 128/888 |
| 5,167,613 | 12/1992 | Karami et al. | 602/57 X |

*Primary Examiner*—Richard J. Apley
*Assistant Examiner*—Kim M. Lee
*Attorney, Agent, or Firm*—Larson & Taylor

[57] ABSTRACT

A wound dressing comprising an absorbent layer (5) and absorbent layer retaining means wherein the absorbent layer retaining means comprises an adhesive annular foam flange (2).

11 Claims, 2 Drawing Sheets

WOUND DRESSING

BACKGROUND OF THE INVENTION

The present invention relates to a wound dressing, to a method of treatment of a wound and to a kit of parts for a wound dressing.

There are many variations of the standard type of wound dressing. The essential features of standard dressings are a wound contacting absorbent material which ideally is non-adherent to the wound, the dressing further comprising adhesive backing means to hold the absorbent material in place.

European Patent Application No. 0236104 discloses a wound dressing comprising a non-adhesive polymer film secured within a foam frame. The frame has a pressure-sensitive adhesive coated on one face, which secures the film to the frame and which extends outwards beyond the film to provide an adhesive surface for securing the dressing to skin around the wound. Preferably there is an absorbent material between the film and the wound. The dressing is designed to overcome the problems encountered with flexible adhesive films; namely the propensity of such films to fold back on themselves thereby self-adhering and the adherence of such films to the margins of the wounds when the dressing is being applied or removed. The frame prevents the film from folding back on itself. Furthermore non-adhesiveness of the film ensures that it does not adhere to the margins of the wound. The frame is dimensioned so that it is of sufficient size to surround the wound without touching the wound margins. Dressings of this kind suffer from the disadvantage that when it is desired to apply a new dressing to the wound, it is necessary to first remove the old dressing. A dressing may need to be removed and replaced by a new dressing several times before the wound has finally healed. Since the dressing is adhered to the skin surrounding the wound, this skin tends to become sensitive and friable with continued removal of the dressing.

A problem with most conventional dressings to a greater or lesser extent, is the tendency for the edge of the dressing to lift away from the skin during use. This failure of the edge seal commonly referred to as 'lift-off' is particularly prone to occur when the dressing is on a part of the body which tends to experience a large degree of friction e.g. the buttocks, the elbows, knees and other such areas which tend to project and which if for example the person is bed-ridden come into constant contact with the bed. It will be appreciated that failure of the edge seal is highly undesirable for a number of reasons. Thus where the dressing has lifted away from the skin, it no longer provides an intact cover over the wound. This enables wound exudate to escape and potentially cause soiling of bedding and/or clothes. More importantly lifting of the dressing enables water and/or bacteria to reach the wound, either of which occurrences is highly undesirable.

A further problem associated with the use of conventional dressings is that where the area to be treated requires a number of dressing changes before healing of the wound has occurred, the skin may become sensitive due to the repeated removal of an adhesive article. Problems of this nature can become quite severe, in particular in already compromised persons.

Thus the object of the present invention is to overcome the above problems, namely to provide a dressing which can be reliably secured to the person by overcoming the problem of breakage of edge-seal and/or which enables an absorbent layer to be repeatedly removed from a person without causing the skin to become sensitised, even when the person is in a compromised state.

SUMMARY OF THE INVENTION

According to the present invention there is provided a wound dressing comprising an absorbent layer and an absorbent layer retaining means wherein the absorbent layer retaining means comprises a flange having an adhesive skin-facing surface and an opposed non-skin facing surface; which flange comprises an inner and an outer perimeter and wherein the absorbent layer is releasably attached to the non-skin facing surface of the flange by attachment means, characterised in that said flange comprises a foam.

DETAILED DESCRIPTION OF PREFERRED EMBODIMENTS

The present invention further provides a method of treatment of a wound comprising securing a wound dressing comprising an absorbent layer and an absorbent layer retaining means wherein the absorbent layer retaining means comprises a flange having an adhesive skin-facing surface, an opposed non-skin facing surface, and inner and outer perimeters, and wherein the absorbent layer is releasably attached to the non-skin facing surface of the flange by attachment means, to the skin of the mammal to be treated.

In a further embodiment there is provided a method of treatment of a wound comprising securing an adhesive flange comprising an adhesive skin-facing surface, an opposing non-skin facing surface, and inner and outer perimeters, to the skin of the mammal to be treated, and subsequently attaching thereto an absorbent layer which absorbent layer comprises a skin-facing surface and a flange-facing portion using an attachment means.

In a yet further embodiment of the present invention there is provided a method of treatment comprising securing a flange comprising an adhesive skin-facing surface, an opposing non-skin-facing surface, and inner and outer perimeters, to the skin of the mammal to be treated, and subsequently attaching to the flange an absorbent layer using an attachment means; the absorbent layer consisting of a core region, and the attachment means comprising an adhesive film.

The dressing of the present invention may be packaged in a suitable bacteria and moisture-proof packaging device.

The present invention further provides a method of manufacture of the dressing comprising forming a flange having a skin-facing surface, a non-skin-facing surface, and inner and outer perimeters, covering the skin-facing surface with an adhesive layer either or before or after forming the flange, and thereafter attaching an absorbent layer to the non-skin-facing surface of the flange.

The absorbent layer may be so dimensioned, such that its perimeter is substantially greater in size than the inner perimeter of the flange, the shape of the absorbent layer being either the same as or different from the area defined by the inner perimeter of the flange. The portion of the absorbent layer which extends beyond the inner perimeter of the flange, will hereinafter be referred to as the overlap region. The overlap region comprises a flange-facing surface and an opposed non-flange facing surface. Preferably the overlap region is integral with the non-overlapping portion of the absorbent layer, the latter hereinafter being referred to as the core region.

In this embodiment the perimeter of the absorbent layer may extend as far as, but not beyond the outer perimeter of the flange. Thus, in the latter case, the outer perimeter of the flange and the perimeter of the absorbent layer may be co-terminous. Thus the outer perimeter of the flange defines the maximum area of the skin-facing surface of the absorbent layer.

Alternatively the absorbent layer may be so dimensioned, such that the perimeter of the absorbent layer is substantially equal in size and shape to the inner perimeter of the flange. Thus the flange fits snugly around the absorbent layer, there being substantially no space between the absorbent layer and the flange. It will be clear that in the embodiment wherein the flange fits snugly around the absorbent layer, that the absorbent layer may or may not possess an overlap region as described above. Preferably the absorbent layer does not comprise an overlap region.

The minimum area of the skin-facing surface of the absorbent layer may be substantially defined by the inner perimeter of the flange. Clearly the area of the absorbent layer may have any value between the maximum and minimum areas discussed above.

The flange may have any desired shape or size, depending on the shape and size of the wound to be treated.

Aptly the flange may for example be square, round, oval, rectangular, sacral, teardrop or U-shaped.

The inner and outer perimeters of the flange may, delimit differently shaped areas, thus for example the inner perimeter may be rectangular, thus defining a rectangular area whereas the outer perimeter may be oval or round in shape, thus defining an oval or disc-shaped area. It will be clear that the outer perimeter's dimensions will be such as to surround the inner perimeter. Aptly the inner and outer perimeters delimit areas of the same shape, the area defined by the outer perimeter encompassing that defined by the inner perimeter.

Aptly the size of the flange is such that the inner perimeter is greater than the perimeter of the wound to which the dressing is to be applied. This ensures that the dressing may be positioned such that the adhesive skin-facing surface of the flange surrounds, but does not contact the wound.

The dressing further comprises an attachment means the purpose of which is to enable the absorbent layer to be releasably attached to the non-skin facing surface of the flange. Where the absorbent layer comprises an overlap region, the attachment means, may be an adhesive layer intermediate the flange-facing surface of the overlap region and the non-skin facing surface of the flange. The absorbent layer retaining means may alternatively be a thin moisture vapour permeable polymeric film having an absorbent-layer facing surface. The film overlies the non-skin facing surface of the absorbent layer and extends beyond the perimeter of the absorbent layer. Preferably the polymeric film has an adhesive layer on its absorbent layer facing surface. Thus preferably the polymeric film is an adhesive polymeric film. Ideally the film is comformable. A preferred adhesive polymeric film is a polyurethane film, such as that known as OPSITE (Trade Mark), available from Smith & Nephew. Less suitably a non-adhesive polymeric film may be used. If a non-adhesive film is used, it is adhered to the non-skin facing surface of the flange by means of an adhesive layer.

It is however preferred that the polymer film attachment means be an adhesive film so that removal of the film from the surface of the flange causes the simultaneous removal of the attached absorbent layer, thus allowing the absorbent layer to be either partially or completely removed by a single pulling action.

It will be appreciated from the above, that where the absorbent layer does not comprise an overlap region, the attachment means comprises a polymeric film.

The distance between the inner and outer perimeters of the flange ie. the width of the flange should be sufficiently dimensioned so as to provide a support for attachment thereto of the absorbent layer by the attachment means.

It will be clear to the skilled man that the tenacity with which the dressing of the present invention will be adhered to the skin is dependent on a number of inter-related factors. These factors include the peel strength of the adhesive, the overall surface area of the adhesive skin-facing-surface of the flange and the amount of adhesive present on the adhesive skin-facing side of the flange ($gm^{-2}$).

Thus assuming the peel strength and amount of adhesive per unit area remain constant, by increasing the surface area of the adhesive skin-facing surface of the flange, the tenacity with which the dressing is attached to the skin will be increased. The presence of the flange thus enables for example a pressure sensitive adhesive of lower strength than would otherwise be necessary to adhere the dressing of the present invention to the skin. By low strength is meant an adhesive which would in the absence of the flange, fail to secure an equivalent absorbent layer to that of the dressing of the present invention.

The differences in the tenacity of the bond between the flange and the skin and the bond between the absorbent layer and the flange be referred to as differences in the stripping load required to remove the flange from the skin and the stripping load required to remove the absorbent layer from the flange.

It will be clear that the stripping load required to remove the flange from the skin, will be greater than the stripping load required to remove the absorbent layer retaining means from the flange. This ensures that the absorbent layer retaining means may be removed from the non-skin facing surface of the flange, without detachment of the flange from the skin.

Suitably the stripping load required to separate the flange from the skin is at least 25% greater, more suitably at least 50% greater and preferably at least 100% greater than the stripping load required to remove the absorbent layer from the flange. Suitably the stripping load required to separate the flange from the skin is from 5 to 25 gf/cm, more suitably is 8 to 20 gf/cm and is preferably 10 to 18 gf/cm. The stripping load may be measured by the procedure described hereinafter.

The stripping load required to remove the absorbent layer from the flange may be measured by taking a sample of the absorbent layer about 200 mm×25 mm having an attachment means removing the release liner and adhering the sample by means of the attachment means to a metal plate. A standard 2 Kg roller is passed three times along the strip and the sample allowed to relax for 5 minutes after rolling. The plate is gripped by the lower jaw of a tensile testing machine. A short length of the absorbent layer is peeled back through 180° so that it may be attached to the upper jaw. The sample is peeled at a rate of 300 mm/min. The results are expressed as average peel force per unit width.

The stripping load may be defined as the average load per unit width of bond line required to separate progressively one layer from another at a separation angle of (approximately) 180° and at a separation rate of 300 mm/min. It is expressed as grams force per cm of width. The stripping load is best measured on a sample of adhesive sheet material prior to forming it into a product.

The stripping load required for removal of the flange from the skin may be measured by stripping the flange using the method described above. It will be appreciated that this is only an approximation of the stripping load required to remove the flange from the skin, it not being possible to measure the latter directly.

The flange may be made from any suitable foam material comformable to body contours. In a preferred embodiment of the present invention, the flange comprises a conformable foam.

The moisture vapour permeability of the flange and adhesive layer on its skin-facing surface should be such that maceration of the underlying skin is avoided. Thus ideally the flange should have a moisture vapour permeability (MVP) when in contact with water vapour but not liquid water, of at least 300 gm$^{-2}$ 24 h$^{-1}$ at 37.5° C. at 100% to 10% relative humidity difference.

The MVP as determined in contact with water vapour but not liquid water is determined as follows:

Discs of the material under test are clamped over Payne Permeability Cups (flanged metal cups) using sealing rings and screw clamps. The exposed surface area of the test sample is 10 cm$^2$. Each cup contains, approximately 10 ml of distilled water.

After weighing, the cups are placed in a fan assisted electric oven which is maintained at 37±1° C. The relative humidity within the oven is maintained at approximately 10% by placing 1 Kg of anhydrous 3-8 mesh calcium chloride on the floor of the oven.

The cups are removed after a predetermined period of time, allowed to cool for 20 minutes and re-weighed. The MVP of the test material is calculated from the weight loss and expressed in units of gm$^{-2}$ 24 h$^{-1}$ at 37.5° C. at 100% to 10% relative humidity difference.

The flange comprises a foam. The foam may be made from any suitable polymer for example a polyester, a polyether, a polyolefin or a polyurethane. Preferably the foam is an open cell breathable foam, since most closed cell foams will not have the required MVP. The foam should be non-absorbent or poorly absorbent, as accumulation of aqueous fluid in the flange is undesirable.

In a preferred embodiment, the foam is a polyurethane foam.

A suitable open cell polyurethane foam is available from PORVAIR.

The distance between the skin-facing surface of the flange and the non-skin facing surface, which will be referred to as the thickness of the flange, may be uniform across the width of the flange. Alternatively the thickness of the flange may vary from one point to another. The variation of thickness is preferably continuous, with the thickness increasing gradually from the outer perimeter to the inner perimeter ie. bevelled. A bevelled flange imparts a better profile to the dressing, diminishing the risk of 'lift-off' of the dressing from the skin by friction. Bevelling of the flange may be achieved cutting, heating, for example, using a hot press or radio-frequency (RF) treatment.

The surfaces of the flange substantially perpendicular to the skin facing surface will be referred to as the side surfaces; the flange having an inner and outer side surface. The inner side surface being adjacent to the inner perimeter and the outer side surface being adjacent to the outer perimeter. It is preferred that the outer side surface is sealed to render it impervious to water. Sealing may be achieved by, for example, by using a hot press or by RF welding. Additionally the non-skin facing surface of the flange preferably has a moisture vapour permeable backing film adhered to its surface to render it moisture and bacteriaproof. Such films should be conformable, and have a MVP of at least 300 gm$^{-2}$24 h$^{-1}$. Examples of suitable backing films are any of the conformable films disclosed in WO 91/01707. The backing layer may also comprise a moisture vapour transmitting adhesive layer to bond the backing layer to the foam. Suitable adhesives for this purpose are also disclosed in WO 91/01807.

The flange has an adhesive means and an adhesive layer on its skin-facing surface. The adhesive may be a continuous or non-continuous layer of a pressure sensitive adhesive. In a preferred embodiment, the adhesive layer extends over the entire skin-facing surface of the flange. Alternatively, the adhesive means may be an adhesive border which extends over part of the skin-facing surface of the flange. The adhesive should be waterproof in both the direction away from the skin and in the direction going towards the skin. Such an adhesive will thus prevent leakage of exudate from the wound and will also prevent possible contamination of the wound underlying the dressing, by urine or faeces where the patient may be incontinent. In addition the dressing will permit routine washing procedures. Having such a waterproof adhesive will ensure that the flange may be kept in place for several days. Suitable adhesives which are moisture vapour transmitting as a continuous layer are preferred, including various acrylate ester copolymer and polyvinyl ether pressure sensitive adhesives such as those disclosed in United Kingdom Patent No. 1280631. Favoured pressure sensitive adhesives comprise copolymers of an acrylate ester with acrylic acid for example as disclosed in United Kingdom Application GB 2070631.

A preferred pressure sensitive adhesive comprises a blend of high and low viscosity polyvinyl ethyl ether in particular "adhesive composition A" disclosed in British Patent No. 1280631. Another preferred pressure sensitive adhesive, disclosed in United Kingdom Application No. 2070631, is a copolymer of 47 parts by weight 2-ethy-hexylacrylate, 47 parts by weight butyl acrylate and 6 parts acrylic acid, polymerised in acetone.

The absorbent layer of the dressing of the present invention may be any of the absorbent materials conventionally used in wound dressings. Suitably the absorbent layer is less rigid that the flange. Thus suitable absorbent materials include hydrogels formed from either natural or synthetic polymers or mixtures thereof. Examples of natural polymers are the cellulosics, alginates or agar. Examples of suitable synthetic polymers include polyisobutylene.

In a preferred embodiment the absorbent layer comprises a conformable foam. Suitable foam include polyacrylate, polyurethane or polyester foams. Preferably the foam is a hydrophilic polyurethane foam. A preferred foam is the hydrophilic polyurethane foam disclosed in European Patent No. EP 0099748. An especially preferred foam, is the absorbent foam dressing known as ALLEVYN (Trade Mark) available from Smith & Nephew. A further suitable material for use as the absorbent layer is carboxylated butadiene styrene rubber.

Still other materials suitable for use as the absorbent layer are woven or non-woven materials. A suitable non-woven is, for example, the standard wound dressing material gauze.

The absorbent layer may have an adhesive layer on its skin-facing surface. The adhesive may be any of the above described adhesives for use on the skin-facing surface of the flange. The adhesive layer on the skin-facing surface of the flange and on the skin-facing surface of the absorbent layer may be the same; alternatively the adhesive layers may comprise different adhesives and may be a continuous or discontinuous layer. Preferably the adhesive on the skin-facing surface of the absorbent layer is a discontinuous layer.

The adhesive layer may extend over the entire skin-facing surface. Alternatively the adhesive layer does not extend over the entire skin-facing surface and flange-facing surface. Thus for example the adhesive layer may extend over an outer edge margin of the absorbent layer.

The dressing may comprise an additional layer intermediate the absorbent layer and adhesive layer. In a preferred embodiment the additional layer is a discontinuous layer. The discontinuous layer may be a polymeric elastomeric film. Suitable discontinuous layers are disclosed in WO 91/01707.

In a further embodiment the absorbent layer comprises a discontinuous layer over its skin-facing surface. In this embodiment the discontinuous layer does not have an adhesive layer on its skin-facing surface.

The flange, absorbent layer and absorbent layer retaining means may be supplied as individual components of the dressing, to be assembled by the user. Alternatively the absorbent layer retaining means may be integral with either the flange or the absorbent layer; the flange and absorbent layer being supplied as individual components to be assembled by use. In a yet further embodiment, the dressing may be supplied in a ready-to-use form.

Any of the above described adhesive surfaces of the dressing, which in use will be skin contacting, may be covered with a release paper before use, for example, silicone release paper.

The absorbent layer may have a backing layer on the surface opposed to the skin-facing portion. The backing layer may be transparent or coloured. Thus for example the backing layer may be the same colour as the skin of the person to which the dressing is to be applied. The backing layer may be any of the above backing layers disclosed for placing on the non-skin facing surface of the flange.

The present invention will be illustrated by reference to the following Example.

EXAMPLE 1

A flange having an inner perimeter which defines a rectangular shape, the dimensions of which are 10 mm×5 mm, and an outer perimeter which also defines a rectangular shape, the dimensions of which are 15 mm×10 mm is formed from a breathable polyurethane foam known as PERMAIR F (Supplied by PORVAIR, Kings Lynn, Norwich). The thickness of the flange is 0.4 mm; the width of the flange is 2.5 mm. An adhesive layer of composition A disclosed in GB 2070631, is applied to the skin-facing surface of the flange as a pattern spread layer. An absorbent layer having a perimeter which defines a rectangular area, the dimensions of which are 12 mm×8 mm is formed according to Example 1 of WO 91/01706. The absorbent layer thus comprises an overlap region which extends 1.5 mm beyond the inner perimeter of the flange. The aborbent layer thus prepared has an adhesive layer on its skin-facing surface. The absorbent layer is then placed adhesive layer down on the non-skin facing surface of the flange to give the prepared dressing.

The invention will now be described by way of example with reference to the accompanying drawings of which:

Figure 1:
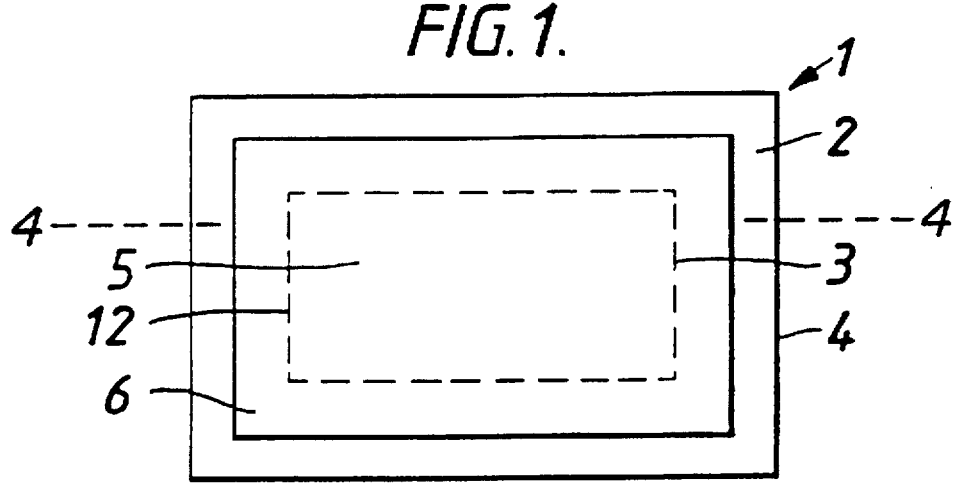
FIG. 1 is a plan view of one type of dressing according to the invention.

The Figures show a view of the non-skin facing surface of the dressing. The dressing 1 of FIG. 1 comprises a flange 2 comprising an inner perimeter 3 and outer perimeter 4; and an absorbent layer 5, the area of which is defined by the inner perimeter of the flange. Attachment means in the form of adhesive film 6 overlies and extends beyond the perimeter 12 of the absorbent layer 5. An adhesive layer 10 on the skin-facing surface of the flange 12 adheres the dressing to the skin.

Figure 2:
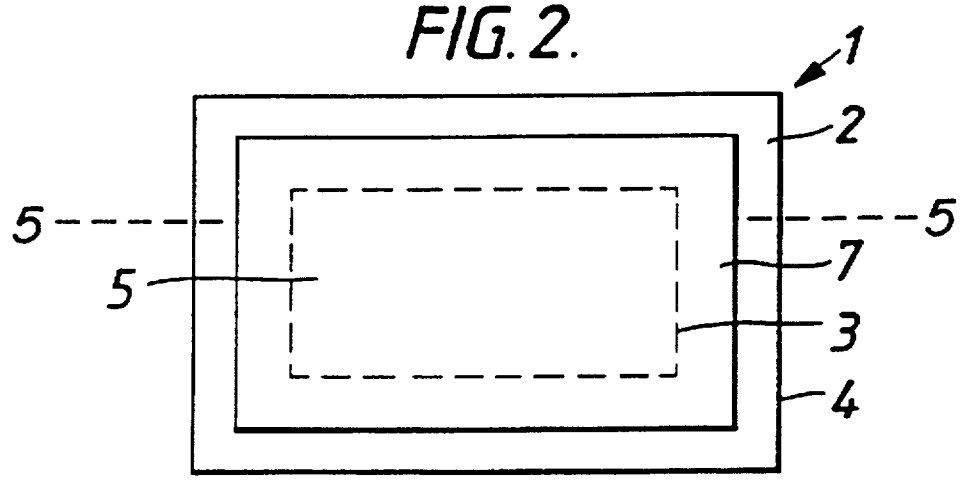
FIG. 2 is a plan view of a further type of dressing according to the invention.

In the dressing 1 of FIG. 2, the aborbent layer 5 comprises an overlap region 7 which extends beyond the inner perimeter 3 of the flange. The overlap region has a flange-facing surface 14. The attachment means comprise an adhesive layer 8 intermediate the flange-facing surface of the overlap region and the non-skin facing surface 9 of the flange. It is also possible that the adhesive layer adheres to the inner perimeter 3 of the flange (not illustrated).

Figure 3:
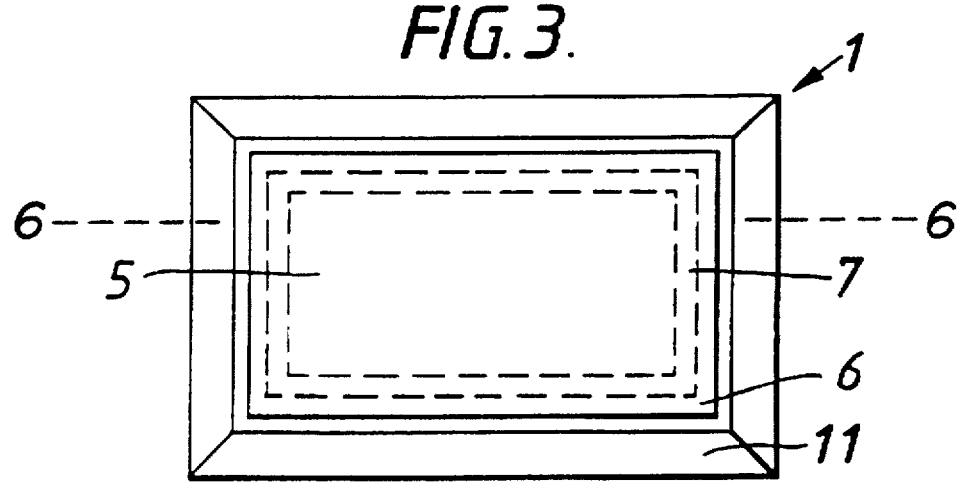
FIG. 3 is a plan view of a further type of dressing according to the invention.

In the dressing 1 of FIG. 3, the absorbent layer 5 extends beyond the inner perimeter of the flange by means of an overlap region as above described in relation to FIG. 2. The overlap region 7, which unlike that of FIG. 2, does not have an adhesive layer on its flange-facing surface 9 is kept in position, by an attachment means in the form of an adhesive film 6 which extends beyond the overlap region 7.

Figure 4:
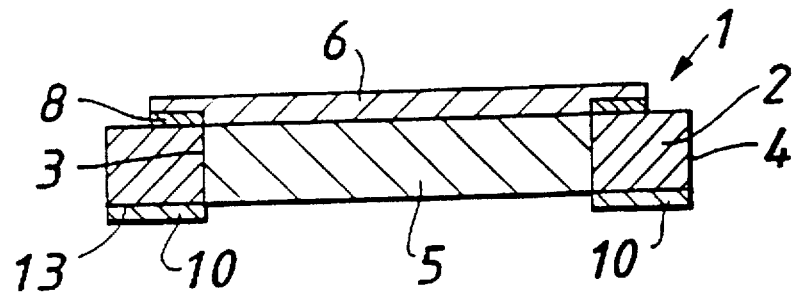
FIG. 4 is a cross-section on the line A—A of FIG. 1.

From FIG. 4, the attachment means in the form of an adhesive layer 8 is clearly visible.

Figure 5:
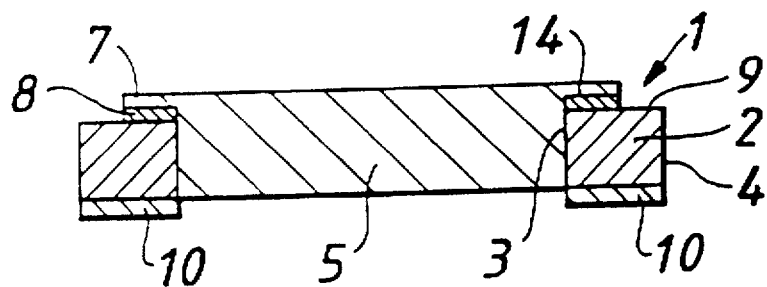
FIG. 5 is a cross-section on the line B—B of FIG. 2.
Figure 6:
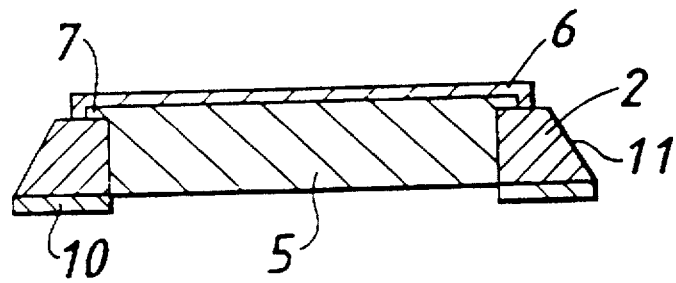
FIG. 6 is a cross-section on the line C—C of FIG. 3.

FIG. 5 and FIG. 6 are similar to FIG. 4 as described above, with the additional feature in FIG. 6, being that the flange has a bevelled edge 11.

In use, the release paper is removed from the flange and the flange is adhered to the subject's skin. During use the absorbent layer may be either partially or completely removed to view the wound. The same absorbent layer may be separated from the flange several times, for example for inspection. After viewing, the absorbent layer may be repositioned on its original position. During use, particularly with highly exuding wounds it may be desirable to remove the absorbent layer in order to replace it with a new absorbent layer. Accordingly the absorbent layer is removed whilst leaving the flange in position. On removal of the absorbent layer, a new absorbent layer may be replaced in the position of the original absorbent layer. Preferably the absorbent layer may comprise an integral absorbent layer retaining means as above described. This step may be repeated as often as is desired. Thus for example in a highly exuding wound it may be desirable to replace the absorbent layer several times, while leaving the flange in position.

We claim:

1. A wound dressing comprising an absorbent layer and an absorbent layer retaining means, said retaining means comprising an annular flange having an adhesive skin-facing surface and an opposed non-skin facing surface, said flange comprising an inner perimeter and an outer perimeter, said absorbent layer being releasably attached to the non-skin facing surface of the flange by attachment means, said flange comprising a foam, said absorbent layer comprising a core region and an overlap region, said overlap region comprising a portion of the absorbent layer which extends beyond the inner perimeter of the flange and overlaps the flange, said overlap region comprising a flange-facing surface, and wherein the attachment means comprises an adhesive layer intermediate the flange-facing surface of the overlap region and the non-skin facing surface of the flange.

2. A wound dressing comprising an absorbent layer and an absorbent layer retaining means, said retaining means comprising an annular flange having an adhesive skin-facing surface and an opposed non-skin facing surface, said flange comprising an inner perimeter and an outer perimeter, said absorbent layer being releasably attached to the non-skin facing surface of the flange by attachment means, said flange comprising a foam, said attachment means comprising a film having an absorbent-layer-facing surface, said absorbent-layer-facing surface having an adhesive layer in contact therewith.

3. A wound dressing as claimed in claim 1 wherein the flange further comprises a moisture vapor-permeable backing film adhered to said non-skin facing surface of said flange.

4. A wound dressing as claimed in claim 1 wherein the absorbent layer comprises a foam.

5. A wound dressing as claimed in claim 4 wherein the absorbent layer foam comprises a hydrophilic polyurethane foam.

6. A wound dressing comprising an absorbent layer and an absorbent layer retaining means, said retaining means comprising an annular flange having an adhesive skin-facing surface and an opposed non-skin facing surface, said flange comprising an inner perimeter and an outer perimeter, said absorbent layer being releasably attached to the non-skin facing surface of the flange by attachment means, said flange comprising a foam, said absorbent layer having a skin-facing surface and an opposed non-skin facing surface, said skin-facing surface of the absorbent layer having an adhesive layer in contact therewith.

7. A wound dressing as claimed in claim 6 wherein the dressing further comprises a discontinuous layer intermediate the absorbent layer and adhesive layer.

8. A wound dressing as claimed in claim 1 having a moisture vapor permeability when in contact with moisture vapor of at least 300 gm$^{-2}$24 h$^{-1}$ at 37° C. at 100% to 10% relative humidity difference.

9. A method of treatment of a wound comprising securing to skin surrounding a wound an annular foam flange, said flange comprising an adhesive skin facing surface, an opposed non-skin facing surface, an inner perimeter, and an outer perimeter, and subsequently releasably attaching to said foam flange an absorbent layer, said absorbent layer comprising a core region and an overlap region, said overlap region comprising a portion of the absorbent layer which extends beyond the inner perimeter of the flange and overlaps the flange, said absorbent layer being releasable attached to said foam flange by providing an adhesive layer intermediate the flange-facing portion of the absorbent layer and the non-skin facing surface of the flange.

10. A method of treatment of a wound comprising securing to skin surrounding the wound an annular foam flange comprising an adhesive skin-facing surface, an opposing non-skin facing surface, an inner perimeter, and an outer perimeter, and subsequently releasably adhesively attaching to the flange an absorbent layer.

11. A kit of parts comprising: an annular foam flange having an adhesive skin facing surface, an opposed non-skin-facing surface, an inner perimeter, and an outer perimeter; and one or more absorbent layer portions, each absorbent layer portion being substantially adapted in size to be releasably adhesively attached to the flange by releasable attachment means.

* * * * *

UNITED STATES PATENT AND TRADEMARK OFFICE
CERTIFICATE OF CORRECTION

PATENT NO. : 5,792,089
DATED : August 11, 1998
INVENTOR(S) : PENROSE et al.

It is certified that error appears in the above-indentified patent and that said Letters Patent is hereby corrected as shown below:

ON THE TITLE PAGE , ITEM [86], SHOULD READ :
-- [86] PCT No.: PCT/GB94/00764
       Section 371 Date: January 26, 1996
       Section 102(e) Date: January 26, 1996

Signed and Sealed this

Eleventh Day of May, 1999

Attest:

Attesting Officer

Q. TODD DICKINSON

Acting Commissioner of Patents and Trademarks